US00RE36415E

United States Patent [19]

McKenna

[11] E Patent Number: Re. 36,415

[45] Reissued Date of Patent: *Nov. 30, 1999

[54] X-RAY TOMOGRAPHY SYSTEM WITH GANTRY PIVOT AND TRANSLATION CONTROL

[75] Inventor: Gilbert W. McKenna, Revere, Mass.

[73] Assignee: Analogic Corporation, Peabody, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/924,281

[22] Filed: Sep. 5, 1997

Related U.S. Patent Documents

[64] Patent No.: 5,448,607
Issued: Sep. 5, 1995
Appl. No.: 08/193,562
Filed: Feb. 8, 1994

[51] Int. Cl.[6] ..... A61B 6/04

[52] U.S. Cl. ..... 378/4; 378/193; 378/195; 378/198

[58] Field of Search ..... 378/146, 195–198, 378/4, 15, 17, 19, 20, 193

[56] References Cited

U.S. PATENT DOCUMENTS

| | | | |
|---|---|---|---|
| 3,924,131 | 12/1975 | Hounsfield | 250/360 |
| 3,983,398 | 9/1976 | Boyd | 250/445 |
| 4,097,744 | 6/1978 | LeMay | 250/366 |
| 4,131,802 | 12/1978 | Braden et al. | 378/4 |
| 4,316,091 | 2/1982 | Bernardi | 378/17 |
| 4,426,715 | 1/1984 | Baer et al. | 378/4 |
| 4,914,682 | 4/1990 | Blumenthal | 378/20 |
| 4,928,283 | 5/1990 | Gordon | 378/4 |
| 5,109,397 | 4/1992 | Gorden et al. | 378/4 |
| 5,218,623 | 6/1993 | Toki et al. | 378/20 X |
| 5,367,552 | 11/1994 | Peshmann | 378/57 |
| 5,404,293 | 4/1995 | Weng et al. | 364/413.19 |
| 5,430,783 | 7/1995 | Hu et al. | 378/15 |
| 5,499,283 | 3/1996 | Toki | 378/15 X |
| 5,638,419 | 6/1997 | Ingwersen | 378/4 |

FOREIGN PATENT DOCUMENTS

| | | |
|---|---|---|
| 8703190 | 8/1988 | Germany . |
| 8703190 U | 8/1988 | Germany . |
| 3808321 | 9/1989 | Germany . |
| 4216983 | 12/1993 | Germany . |
| 56-148340 | 11/1981 | Japan . |
| 60-174138 | 9/1985 | Japan . |
| 61-209640 | 9/1986 | Japan . |
| 2-45714 | 3/1990 | Japan . |
| 2-121634 | 5/1990 | Japan . |
| 2-121637 | 5/1990 | Japan . |
| 3-36611 | 4/1991 | Japan . |
| 3-107905 | 11/1991 | Japan . |

OTHER PUBLICATIONS

Crawford, Carl R., et al., "Computed Tomography Scanning with Simultaneous Patient Translation," Medical Physics, vol. 17, No. 6, Nov./Dec.

Crawford, Carl R., et al., "Moving Beam Helical CT Scanning," IEEE Transactions on Medical Imaging, vol. 15, No. 2, Apr. 1996, pp. 188–196.

*Primary Examiner*—David P. Porta
*Attorney, Agent, or Firm*—Lappin & Kusmer, LLP

[57] ABSTRACT

An improved, portable X-ray tomography system is disclosed wherein lateral movement of the various tomography components relative to a stationary patient during a scanning procedure is precisely controlled by mechanical displacement means which, in tarn, is coupled to electro-mechanical means for simultaneously measuring and monitoring the amount of the displacement.

58 Claims, 6 Drawing Sheets

X-RAY TOMOGRAPHY SYSTEM WITH GANTRY PIVOT AND TRANSLATION CONTROL

Matter enclosed in heavy brackets [ ] appears in the original patent but forms no part of this reissue specification; matter printed in italics indicates the additions made by reissue.

RELATED APPLICATIONS

This application is related to U.S. patent application Ser. No. 08/193,783, filed in the name of Gilbert W. McKenna and entitled "X-ray Tomographic Scanning System" (Attorney's Docket No. ANA-30); U.S. patent application Ser. No. 08/193,696, filed in the name of Gilbert W. McKenna and Ronald E. Swain and entitled "Tomographic Scanner Having Center of Rotation for all Physics" (Attorney's Docket No. ANA-31); and U.S. patent application Ser. No. 08/193,782, filed in the name of Gilbert W. McKenna and entitled "Stabilized, Cantilevered, Patient Trauma Table System" (Attorney's Docket No. ANA-58), all filed simultaneously herewith and assigned to the present assignee.

FIELD OF INVENTION

The present invention relates generally to X-ray tomography Systems and, more specifically, to a portable system for supporting and moving a tomography gantry assembly relative to a stationary support for supporting the object being canned in order to provide limited, precisely controllable and measurable translation of the gantry assembly parallel to the stationary support, and also to provide limited, precisely controllable tilting of the gantry assembly relative to the object being scanned.

BACKGROUND OF THE INVENTION

The present invention is an improvement in portable X-ray tomography systems such as those described in U.S. Pat. Nos. 4,928,283 (issued May 22, 1990 to Bernard M. Gordon for X-Ray Tomography Apparatus, and assigned to the present assignee) and 5,109,397 issued Apr. 28, 1992 to Bernard M. Gordon et al. for X-Ray Tomography Apparatus With Lateral Movement Compensation, also assigned to the present assignee); and helical scan tomography systems such as described in German Gebrauchsmuster File No. G 87 03 190.6, filed by Siemens AG and published Aug. 11, 1988, all three documents being incorporated herein by reference.

Tomography systems have been used for many years to create images of cross-sectional slices through object, and are particularly used as a diagnostic aid. CT (computed tomography) scan systems usually include a gantry assembly comprising a disk mounted for rotation within a gantry frame. In third generation machines, the disk supports X-ray imaging components including an X-ray source and X-ray detectors that rotate within a stationary frame. In fourth generation machines the X-ray detectors are secured equiangularly around the stationary frame while the source rotates with the disk relative to the detectors. In both types of systems, the source may provide periodic X-ray pulses, or alternatively, continuous-wave (CW) X-rays. The disk of the gantry is normally adapted to rotate through a full 360° rotation so that the imaging components secured to the disk rotate through a plurality of incremental positions where a corresponding series or set of readings (called "views") by the detectors are made. The number of photons absorbed along the various paths through the object, during each sampling period defining each view or set of readings is a function of the absorption characteristics of the portions of the object along each path during each set of readings. Thus, a plurality of views are taken through the portion of an object disposed within the common plane of rotation of the X-ray paths (hereinafter the "scanning plane"). The detectors generate a corresponding plurality of analog information signals representative of X-ray flux detected by the detectors during each sampling period or projection view.

The output analog information signals of the X-ray detectors acquired from all of the views of the 360° rotation, i.e., through all of the incremental angular positions of the 360° rotation within the scanning plane, are processed, typically through a back projection processing technique, so as to create an image of the slice of the interior structure of the object exposed to the X-rays: In some CT scanners, provision is made to move the patient support while performing a scan in order to provide a helical scan so as to increase the scanned volume.

An important consideration in CT scanning has always been the accurate and consistent alignment of the tomography components and the patient both throughout the rotation and over the course of many scans and patients. Misalignment or movement can negatively influence the data of an entire scan. In order to deal with this factor, manufacturers of prior art CT scan apparatus typically have produced a very large and massive machine which includes a heavy gantry assembly for supporting the tomography components. The handling of this weight requires additional mass in the remainder of the apparatus and typically a large apparatus overall. The rotating disk supporting at least the X-ray source is typically rotatably supported in a excessive, finely-machined bearing assembly, and an extremely massive and heavy support system is provided for supporting the gantry assembly and tomography components. The very massiveness of these systems helps to minimize vibration and other lateral mechanical movements, which, for example, can occur with wear between parts moving relative to one another.

But such massive systems are also extremely expensive to build and once located and constructed for use are extremely difficult to relocate. They require large amounts of floor space and thus can not be used in space limited environments. Thus, use of such systems, for example, within the operating theater are impractical. The result is that a very powerful data gathering diagnostic system is not readily available to a surgeon when such data might be very helpful, or to trauma units when movement of the patient should be minimized.

One ramification of the extra size and mass of these machines has been to provide a fixed gantry assembly so as to require a movable patient table, as the weight of the patient and the patient table is typically much less than the weight of the gantry assembly and its rotating components. A movable patient table is used not only to properly position the patient in the desired location relative to the fixed gantry assembly so that a scan can be performed through a select portion of the patient's body; but in the case of machines capable of performing helical scans, to move the patient parallel to the rotation axis (referred to as the "Z-axis") of the tomography imaging components, while the components are rotating about the patient. But, the apparatus which has resulted from these various requirements has been typically large, heavy, expensive, and difficult to relocate. It has required a large amount of floor space and thus can not be used in space-limited environments. A further disadvantage caused by the size and weight of these apparatuses has been the wear experienced in the moving parts thereof. Moreover, in the course of repositioning a movable patient table for successive scans or a helical scan, the momentum of the movement of the table can result in patient movement during the scan resulting in erroneous scanning data. This problem can be especially acute when the table moves abruptly at the beginning or end of a scan.

At least one three dimensional CT scanning system has been suggested in German Gebrauchsmuster File No. G 87 03 1906 (described above) in which the tomographic elements move through a helical path about a stationary patient table. As described in the document, a rotating ring supports the X-ray source and X-ray receiver. The rotating ring is provided with helical screw threads so that as the ring rotates within a shell during a scan it simultaneously moves parallel to the patient table so that the ring moves in a helical manner along the length of the patient table and so that a high three-dimensional volume can be measured. The data acquired during a three dimensional scan male it possible to reconstruct large volume images. However, the movement of the rotating ring is confined to helical movement so that the system is only capable of three-dimensional scanning. Additionally, while the patent suggests that, depending on system design, it is possible to reconstruct images taken during the three-dimensional scanning process for any theoretical rotating ring inclination (layer angle) on the basis of data taken during the scan even through the scanning plane established by the ring can not be-tilted. This would require the ring to be laterally displaced parallel to the orientation of the patient table over a large distance. For example, to obtain data equivalent to a 45° inclined angle, the rotating ring would have to transverse a distance equal to the distance between the source and detectors exposing the patient to excessive amounts of X-rays over a large period of time. Further, the ring appears to be large, and unnecessarily massive. The system therefore would not be practical as a portable system.

The portable tomography apparatus described in U.S. Pat. No. 4,928,283 (Gordon) represents a significant improvement in the state of the art by providing an apparatus with a high degree of mobility. The tomography components are supported on a structure that also serves to support a removable patient table. The gantry assembly is movable between a first position where the table is disposed within the gantry and a scan can be performed on a patient disposed on the patient table and a second position where the gantry assembly is oriented 90° to the first position so that it can be more easily transported and stored. The gantry assembly can be tilted The support structure in the Gordon patent also provides means for rotating the tomography components about the Z-axis and means for moving the tomography components linearly along the Z-axis relative to the table when the tomography components are oriented in the first direction. The patent suggests that the apparatus is thus capable of helical scanning.

The apparatus of the Gordon patent is therefore an improvement over the much larger, essentially immobile tomography systems of the prior art, With the Gordon apparatus, the tomography system can be brought to the patient, for example, instead of vice versa. But, the apparatus of the Gordon patent is still larger and less maneuverable than desired because this apparatus necessarily incorporates the support structure for the patient table. Furthermore, this apparatus requires transferring a patient to the special removable patient table, which inhibits use of the apparatus at critical times such as during surgery, or during emergency situations. In addition, precise control and measurement of the position of the gantry assembly relative to the patient is an elusive problem, since reducing the overall weight and mass of the system increase the amount of vibration and mechanical noise to which the system will be subject as the components rotate during a scan.

U.S. Pat. No. 5,109,397 (Gordon et al.) attempts to overcome some of the problems endemic to a portable tomography system by incorporating means for providing error information at incremental angular positions and means for compensating the data derived from the analog information signals. Another type of measurement system for providing such error information is described in U.S. patent application Ser. No. 08/162,653 filed on Dec. 6, 1993 in the names of Bernard Gordon, et al., for "Apparatus for and Method of Measuring Geometric, Positional and Kinematic Parameters of a Rotating Device" (Attorney's Docket No. ANA-21) and assigned to the present assignee. It remains desirable, nevertheless, to reduce or eliminate misalignment errors in portable tomography systems through more accurate control and measurement of the position and orientation of the tomography components.

It is desirable to provide an improvement over the X-ray system described in U.S. Pat. No. 4,928,283 (Gordon), by providing an improved X-ray tomography system with translation a pivoting control so that precise positioning of the components relative to a stationary patient table can be easily accomplished.

OBJECTS OF THE INVENTION

Accordingly, it is a general object of this invention to provide a tomography apparatus which substantially reduces or overcomes the above-noted problems.

More specifically, it is an object of this invention to provide tomography apparatus with means for precisely controlling and measuring the position of the scanning plane vis-à-vis a stationary patient during a scanning procedure.

Another object of this invention is to provide a portable tomography apparatus with means for precisely controlling and measuring the longitudinal position of the gantry assembly relative to the longitudinal axis of a patient's body or limb.

And another object of this invention is to provide a portable tomography apparatus with means for precisely controlling and measuring the tilting of the gantry assembly relative to the longitudinal axis of a patient's body or limb.

It is also an object of this invention to provide a portable tomography system which is readily adaptable for use with a patient in either a recumbent or a sitting position.

A further object of this invention is to provide a portable tomography system which is independent of the patient support means.

Specifically, it is an object of this invention to provide a portable tomography apparatus wherein lateral translation of the gantry assembly relative to the support structure is regulated by mechanical displacement means which, in turn, is coupled to electro-mechanical means for simultaneously measuring and monitoring the amount of the displacement.

Still another object of this invention is to provide a portable tomography apparatus capable of carrying out either a sequence of precisely controlled individual X-ray scans or a continuous, helical scan.

Other objects of the invention will in part be obvious and will in part appear hereinafter. The invention accordingly comprises the apparatus possessing the construction, combination of elements and arrangement of parts exemplified in the following detailed disclosure and the accompanying drawings, and the scope of the application of which will be indicated in the claims.

SUMMARY OF THE INVENTION

The present invention comprises tomography apparatus wherein limited lateral movement of a gantry assembly relative to a stationary patient is precisely controlled by coupling mechanical displacement means to electro-mechanical means for simultaneously controlling and measuring the amount of the displacement. A support structure for the gantry assembly preferably comprises a cat-like apparatus on wheels being adapted to: support a translatable and pivotable gantry assembly so as to provide limited, precisely controlled and monitored lateral movement of the gantry assembly relative to the patient and the support structure; and limited, precisely controlled tilting of the gantry assembly relative to the axis of a patient's limb or body. The resulting tomography system is compact, readily mobile, and easily maneuverable while at the same time generating highly accurate and dependable scanning data.

BRIEF DESCRIPTION OF THE DRAWINGS

For a fuller understanding of the nature and objects of the present invention, reference should be made to the following detailed description taken in connection with the accompanying drawings wherein.

DETAILED DESCRIPTION OF THE DRAWINGS

Figure 1:
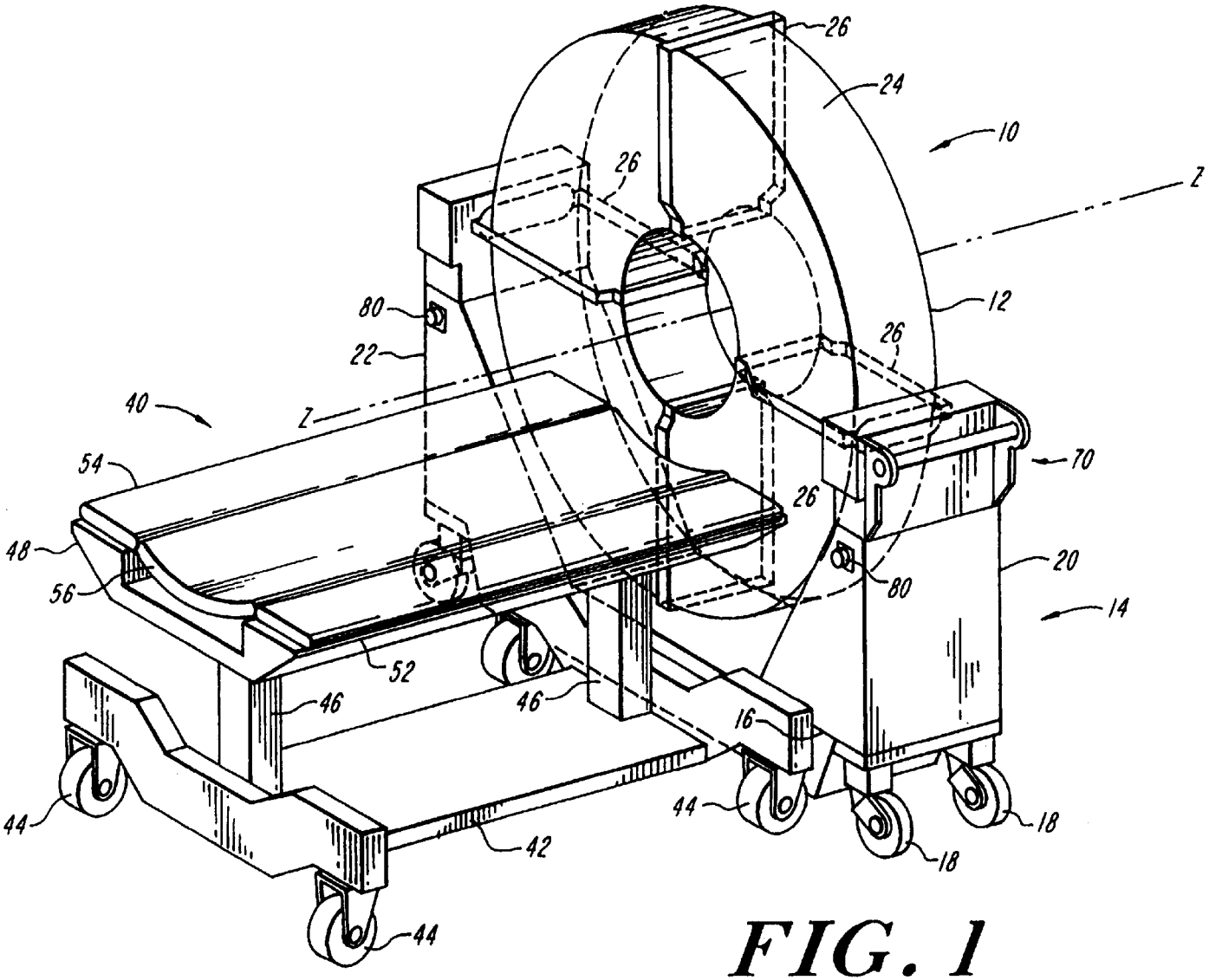
FIG. 1 is a schematic perspective view of the tomography apparatus of the present invention illustrated in relationship to a state patient table.
Figure 2:
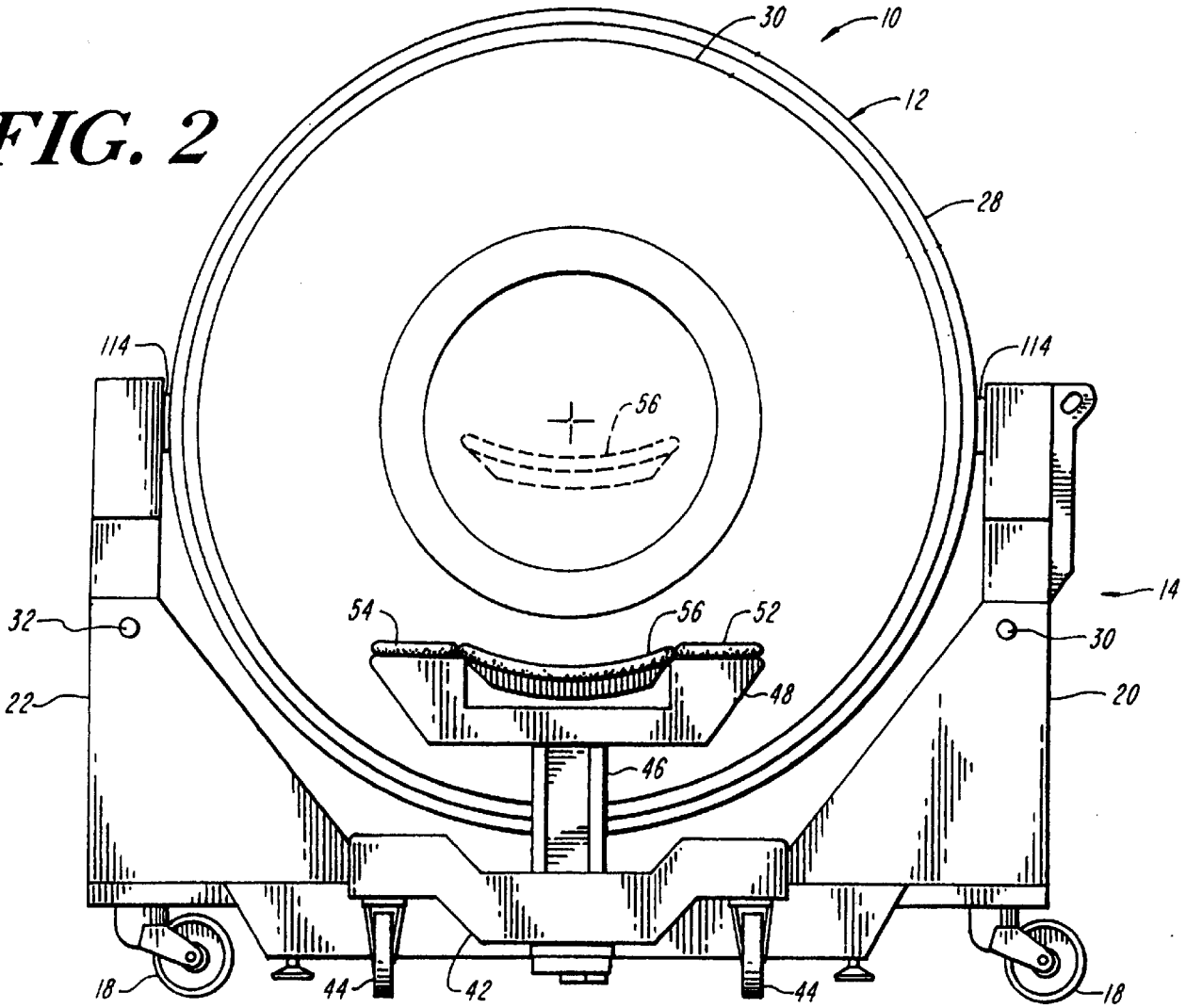
FIG. 2 is a schematic end view of the tomography apparatus and patient table illustrated in FIG. 1.
Figure 3:
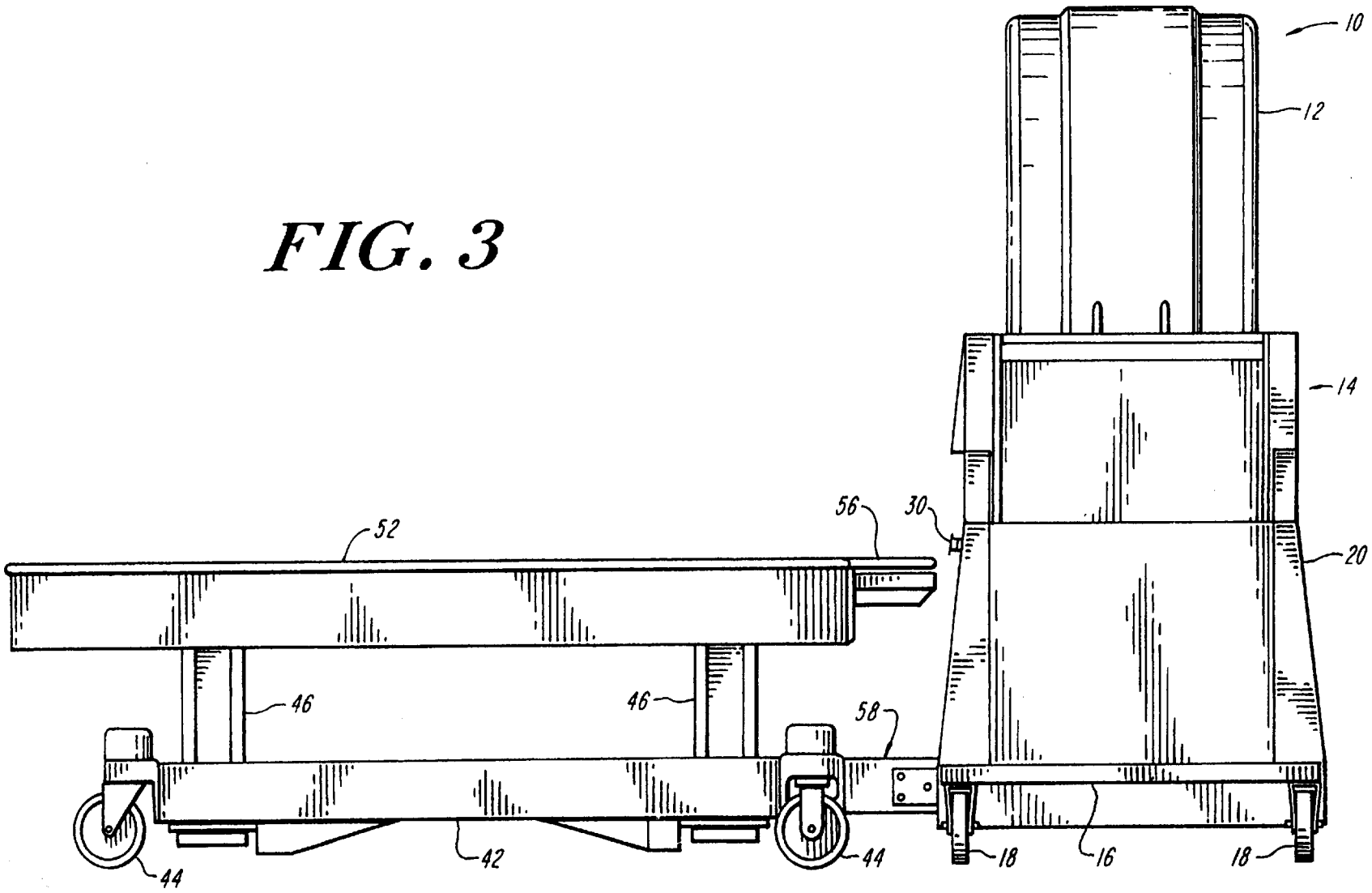
FIG. 3 is a schematic side view of the tomography apparatus and patient table illustrated in FIG. 1.

FIGS. 1–3 show an X-ray tomography apparatus 10 generally including a doughnut-like gantry assembly 12 mounted on a movable cart apparatus 14. As schematically shown in FIG. 2, gantry assembly 12 comprises a stationary annular frame 28, and a disk 30 mounted for rotation within the annular frame 28 and supporting conventional tomography components, typically including an X-ray source, a plurality or array of X-ray detectors diametrically opposite the X-ray source, a power source, and other components as described in U.S. Pat. No. 4,928,283. For additional details relating to the gantry assembly see copending U.S. patent application Ser. No. 08/193,783, filed in the name of Gilbert W. McKenna and entitled "X-ray Tomographic Scanning System" (Attorney's Docket No. ANA-30); and U.S. patent application Ser. No. 08/193,696, filed simultaneously herewith in the name of Gilbert W. McKenna and Ronald E. Swain and entitled "Tomographic Scanner Having Center of Rotation for all Physics" (Attorney's Docket No. ANA-31), assigned to the present assignee, and incorporated herein by reference. In order to protect and conceal the components distributed around the frame of gentry assembly 12, a skin or cover 24 of an X-ray transparent material (shown schematically in FIG. 1), such as a polycarbonate plastic or the like, may be provided and secured in place by a plurality of bands or fasteners 26 distributed around the circumference of the gantry assembly. Means (not shown) are provided for rotating the tomography components mounted on gantry assembly 12, such as the means described in U.S. Pat. No. 4,928,283.

As best seen in FIGS. 1 and 2, cart apparatus 14 is generally of a U-shaped configuration comprising a transverse base member 16 supported on a plurality of wheels 18, upwardly projecting wall members 20 and 22, which may be either extensions of or fastened to base member 16, and means for supporting gantry assembly 12 on wall members 20 and 22. In place of wheels 18, any equivalent multi-directional movement or rolling means, such as ball-and-socket rollers, may be substituted. In a preferred embodiment, wall members 20 and 22 include inwardly sloping lower portions (as best seen in FIG. 2) such that wall members 20 and 22 together with base member 16 comprise a protective cradle for the lower half of gantry 12 which flanks the outer circumferential walls of the gantry assembly. One or both wall members 20 and 22 further comprise a gantry displacement mechanism 70, generally indicated in FIG. 1 (and described in greater detail in connection with FIG. 5), wherein a portion of which is visible as rod members 80, and a gantry tilt control mechanism (not seen in FIGS. 1 and 2, but described in greater detail hereinafter in connection with FIG. 6).

For reference purposes, FIGS. 1–3 also show a separate, movable, X-ray transparent patient table or gurney 40 generally comprising a transverse base member 42 supported on a plurality of wheels 44 in combination with upright support members 46 supported on base member 42 at the lower ends thereof. Members 46 in turn support table means 48 at their upper extremities. It will be appreciated that patient table 40 may instead be stationary, in which case no wheels 44 would be needed, without in any way affecting the operation of the tomography apparatus of this invention. In a preferred embodiment, upright table support members 46 may comprise telescoping tubes or similar means by which the height of the foot and head ends of table means 48 above the floor can be readily and independently adjusted by conventional automated or manual means. Such table height adjustment means facilitates positioning a patient at the center of the tomography apparatus, as better seen in FIG. 2 where the dotted outline of patient support member 56, as described below, indicates the table in the elevated position. In another preferred embodiment, as seen in FIG. 2, table means 48 may comprise two laterally extending, grooved side or rail members 52 and 54 and a flat or curved patient support member 56 adapted along its lateral edges to be slidably engaged by the grooves of members 52 and 54. The table 40 includes a coupling mechanism generally indicated at 58 in FIG. 3. Such a patient table or gurney specially adapted for use in combination with the tomography system of this invention is described in a copending U.S. patent application Ser. No. 08/193,782, filed simultaneously herewith in the name of Gilbert W. McKenna and entitled "Stabilized, Cantilevered, Patent Trauma Table System" (Attorney's Docket No. ANA-58),assigned to the present assignee and incorporated herein by reference.

Thus, in preparation for a CT scan, as best seen in FIGS. 1 and 3, cart 14 carrying gantry assembly 12 and one end of table 40 would be moved together and joined by mechanism 58. Table means 48, if necessary, would be elevated to the desired height for centering with respect to gantry assembly 12. Then, patient support member 56 carrying the subject patient would be slid into the inner, annular region of gantry assembly 12 for generally positioning the patient. Once the patient is thus initially positioned vis-à-vis the tomography apparatus, further movement of the patient or patient table is unnecessary with the apparatus of this invention. Instead, the gantry displacement mechanism 70 is capable of limited, controlled lateral translation of gantry assembly 12 generally along the longitudinal axis of the table in order to generate the sequential X-ray data needed for large volume and helical scan imaging. In one embodiment of this invention, therefore, X-ray imaging is performed stepwise in conjunction with incremental, precisely measured, discrete displacements of the gantry assembly with respect to the patient, which displacements are effected by briefly and repeatedly activating the gantry displacement mechanism. In an alternative embodiment, X-ray imaging can also be carried out continuously as a helical scan by activating the gantry displacement mechanism for gradual, continuous and precisely measured lateral displacement of the gantry assembly while the tomography system is in operation with the disk 30 rotating within the annular frame 28. Although a patient table such as that illustrated in FIG. 1 is particularly well adapted to performing CT scans with the apparatus of this invention, as described above, this invention is not to be construed as being limited in any way to use in combination with patient table 40 as described above. It should be appreciated that the tomography apparatus of this invention has utility with other types of patient tables and with so other types of patient supports, such as a chair as illustrated in FIG. 4.

Figure 4:
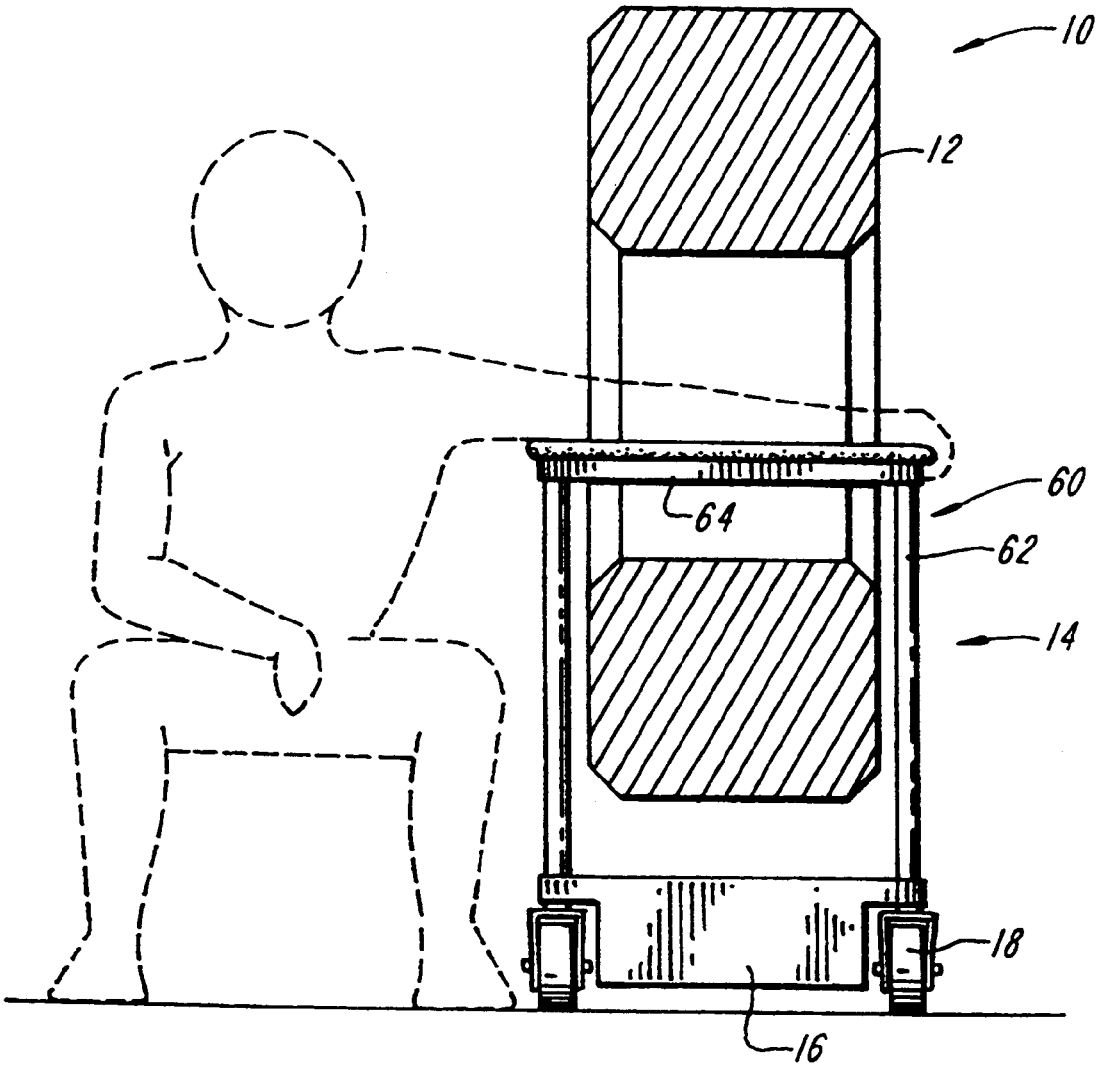
FIG. 4 is a schematic side view of the tomography apparatus, similar to FIG. 3, but shown in use with a patient chair and arm support.

FIG. 4 shows a plan view of an alternative utilization of the tomography apparatus of this invention, again wherein corresponding numbers identify corresponding members. As shown in FIG. 4, limb support means 60, comprising a frame 62 supporting a limb platform 64, is mounted on cart 14. The tomography apparatus thus adapted is suitable for performing CT scans on a patients limb, such as an arm, while the patient sits or reclines alongside can 14.

Figure 5:
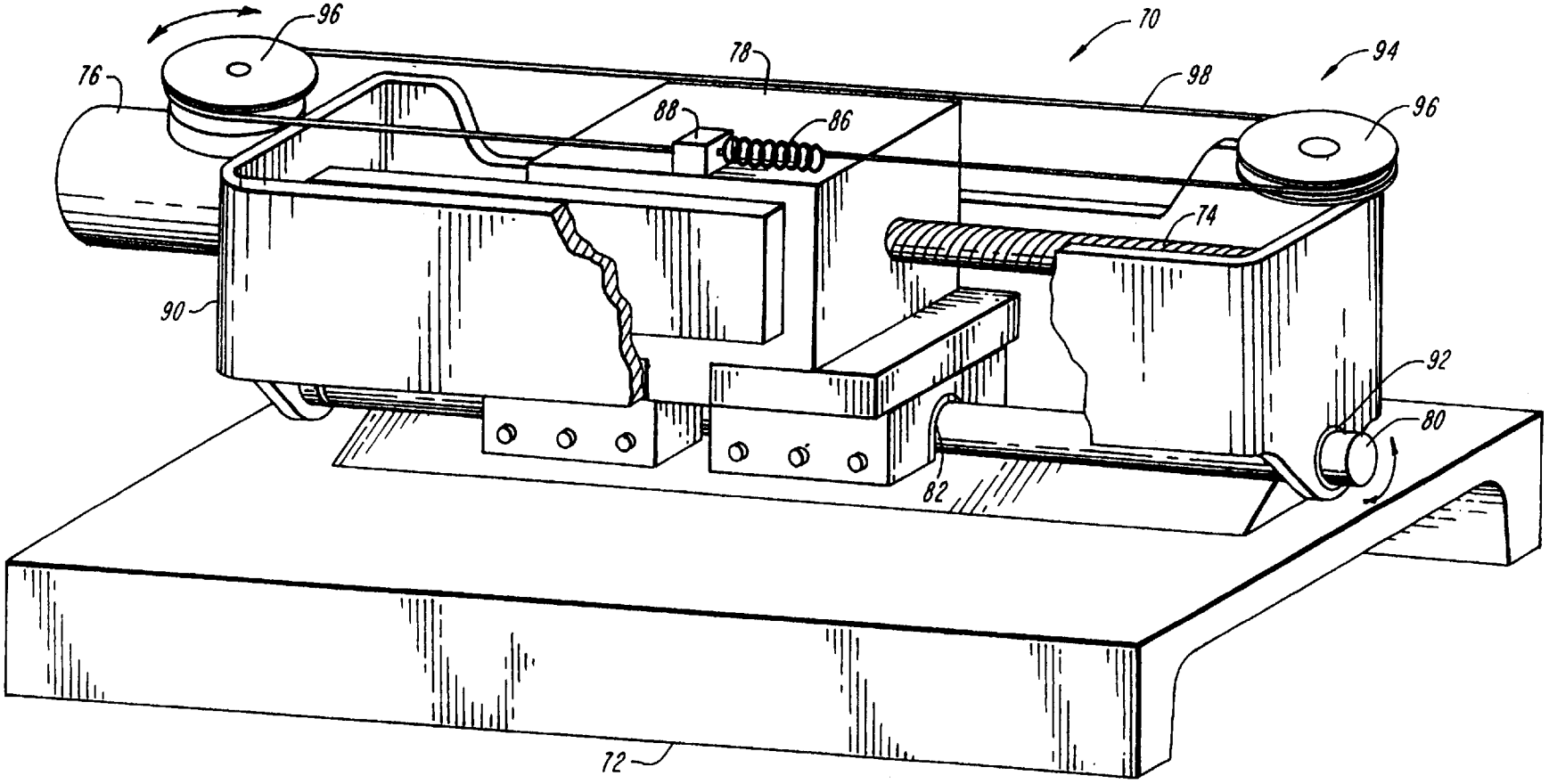
FIG. 5 is an enlarged, schematic, partly cutaway isometric view of the mechanical displacement mechanism used to achieve lateral movement of the gantry assembly and of the associated electro-mechanical system for measuring and monitoring the amount of the displacement.

FIG. 5 shows an enlarged, partially cutaway view of the gantry displacement apparatus as of this invention. Preferably a pair of identical gantry displacement apparatus 70, one being shown in FIG. 5 as being fixed along one side thereof to base or surface member 72 for illustration, are respectively adapted to be incorporated into or secured to the wall members 20 and 22 of cart 14 as described hereinafter. Each displacement apparatus 70 generally comprises an elongated ball screw element 74, connected to drive means such as a reversible drive electric stepping motor 76, and displacement member 78 functioning in cooperation with screw element 74, such as a ball nut, and connected to the gantry assembly 12. Displacement member 78 is adapted for two-way movement along a track generally defined by screw element 74. The movement track has a length that is somewhat less than the width of cart 14. Screw element 74 and the associated displacement member 78 are at least partly enclosed by housing means 90. In one embodiment, electric stepping motor 76 may be mounted externally of one wall of housing means 90 and connected to screw element 74 through an aperture in that housing wall. For example, a stepping motor having 200 steps per five millimeters parts a very fine adjustment resolution of 0.001 inches/step. Housing means 90 may further comprise apertures 92 in two opposite end walls in order to accommodate the opposite ends of a guiding rod member 80 as hereinafter described. As seen in FIG. 5, displacement member 78 comprises an internally threaded block which engages screw element 74 such that, as motor 76 rotates screw element 74 in a clockwise direction, member 78 is moved along the screw element in a first direction, and, as motor 76 rotates screw element 74 in a counterclockwise direction, member 78 is moved along the screw element in a second, opposite direction.

Figure 6:
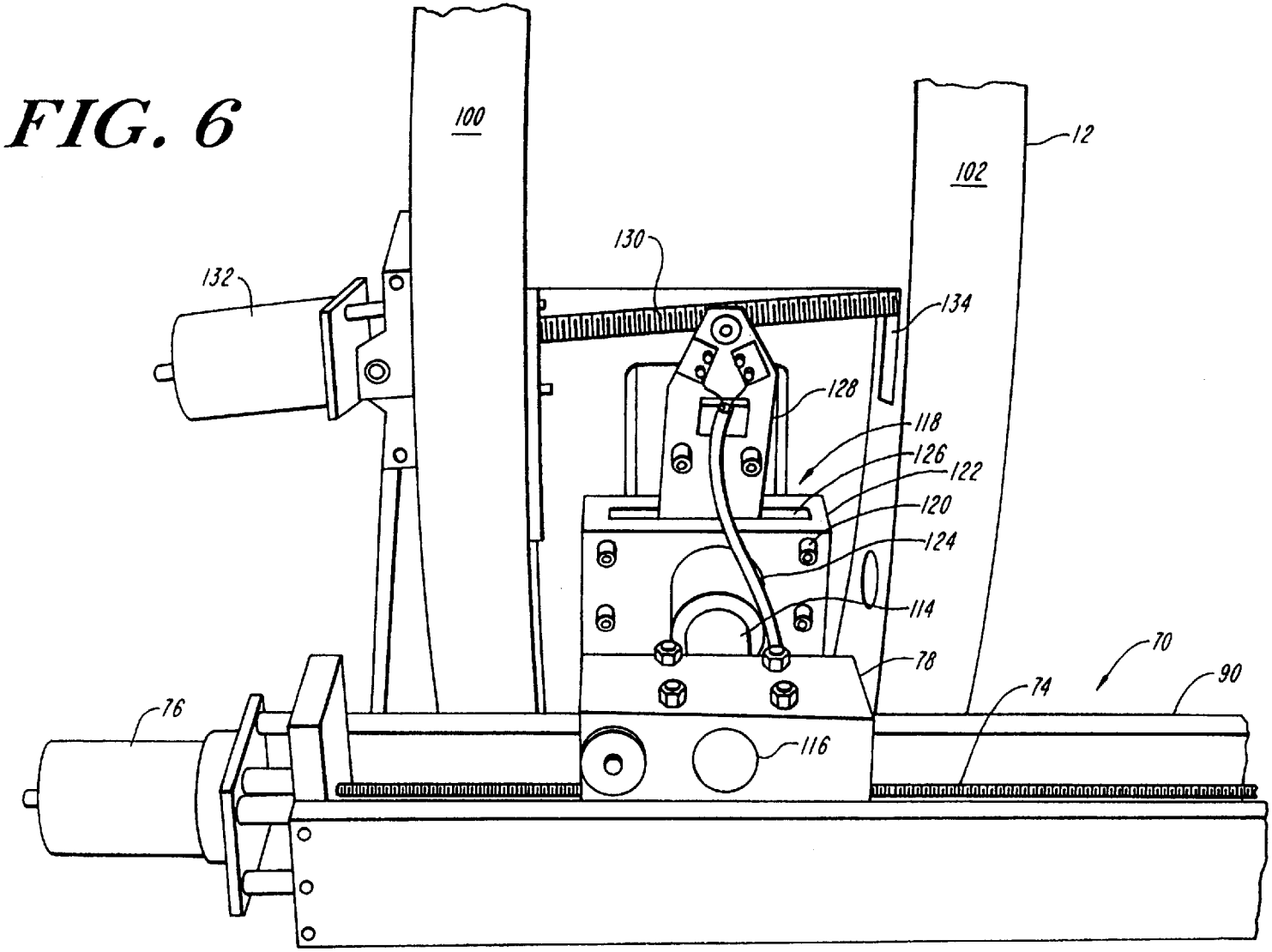
FIG. 6 is an enlarged, schematic, isometric side view of the tomography apparatus of FIG. 1 illustrating the relationship of the mechanical displacement mechanism of FIG. 5 relative to the tomography apparatus and also illustrating the tilt control mechanism of this invention.

The displacement apparatus may further comprise a guiding rod member 80 disposed in a linear bearing comprising a hemispherical or semi-tubular passageway 82 extending through displacement member 78 (which is coupled to the gantry assembly as described in greater detail in FIG. 6), or through another member which is fastened to member 78, wherein the longitudinal axis of the hemispherical passageway 82 is substantially parallel to the longitudinal axis of ball screw 74. The ball screw 74 is suitably journaled in the housing 90 so that it freely rotates in response to the operation of the steps per motor 76 without moving longitudinally. The passageway 82 has a diameter slightly greater than that of rod member 80 and may lubricated or be fitted with ball bearings such that displacement member 78 slides along rod member 80 as ball screw 74 is driven by motor 76. As previously noted, the opposite ends of rod member 80 are further supported by passing through a 92 in two opposite end walls of housing 90. While the two displacement members 78, positioned on respective diametrically opposite sides of the gantry assembly, are preferably oriented parallel to one another, in order to accommodate minor non-parallel misalignments between the two, apertures 92 have diameters slightly larger than that of rod member 80 such that a limited degree of lateral movement or tolerance of rod member 80 is provided in order to accommodate such minor misalignments during the repositioning the tomography apparatus.

Displacement apparatus 70 further comprises means for measuring the amount of any displacement, so that if necessary it can be monitored and/or controlled. In a preferred embodiment, the displacement monitoring means comprises electro-mechanical apparatus, such as a potentiometer 94, suitably biased with a supply voltage (not shown) for providing a voltage output as a function of the position of the displacement member 78. As seen in FIG. 5, potentiometer 94 is secured relative to the surface member 72, preferably at one end of the screw 74. Potentiometer 94 includes a pulley wheel 96 which when turned varies the resistance of and thus the voltage output of the potentiometer 94. A second, follower pulley 96 is preferably secured relative to the surface 72, preferably at the other end of screw 74. A cable 98 is looped around the two pulleys and is fixed at one end by suitable means, such as a cable connector 88, to the displacement member 78 and its other end to a spring 86 for tensioning the cable, said spring 86 also being connected to the displacement member 78, preferably via the connector 38 as illustrated. Extremely precise monitoring of the amount and direction of any movement of displacement member 78 (and thus longitudinal movement of the gantry assembly) is realized by conventional means for monitoring the electrical voltage across the potentiometer. In a preferred embodiment of this invention, a pair of displacement apparatuses 70 as shown in FIG. 5 are respectively incorporated into or mounted on each of wall members 20 and 22 of cart apparatus 14 (FIG. 1) so that both sides of gantry assembly 12 can be moved smoothly and simultaneously.

FIG. 6 shows a schematic side view of gantry assembly 12, with skin 24 removed for illustrative purposes mounted on cart apparatus 14 (FIG. 1) and connected to a gantry displacement apparatus 70 similar to that shown in FIG. 5. As discussed with respect to FIG. 5, in FIG. 6 an elongated ball screw 74 is at least partly housed in housing 90 and is driven by stepper motor 76 mounted externally of housing 90 and connected to ball screw 74 through an aperture in the adjacent wall of housing 90. The ball screw is suitably journaled in the housing 90 so that it freely rotates in response to stepper motor 76. The longitudinal axis of screw element 74 is substantially horizontal and generally parallel to the longitudinal axis of table 40 (shown in FIGS. 1–3) and limb support 64 (shown in FIG. 4). Displacement apparatus 70 further comprises internally threaded displacement member 78, preferably including a ball screw, which engages screw 74 so as to move toward or away from motor 76 inside housing 90 as motor 76 rotates screw element 74 respectively clockwise or counterclockwise.

Each displacement member 78 is fastened to a corresponding arm 114 (seen in FIGS. 2 and 6). As shown in FIG. 6, one end of each arm 114 is mounted in an aperture 116 of member 78 and secured in place. The two arms preferably each have longitudinal axes disposed coaxial with respect to one another. The opposite end of arm 114 is coupled to gantry assembly 12, by means of a fitting assembly 118 located in an uncovered recessional area between the front and rear portions 100 and 102 of the annular frame of the gantry assembly 12 and secured so that the gantry assembly and each fitting assembly 118 arm adapted to pivot about the arms 114. Screws 120 or equivalent means may be used to secure by mount assembly 118 to the frame of the gantry assembly. Fitting assembly 118 comprises box member 122 having a tubular projection 124 with a center aperture adapted to receive the opposite end of pivot arm 114. Lubrication or ball bearings may be provided inside the aperture of tubular projection 124 to facilitate rotation of the gantry assembly 12 about the pivot arm 114. Box member 122 further comprises an elongated slot 126 adapted to receive a fixed-length arm member 128. Member 128 has one end fixed to the pivot arm 114, and its other, upper end, engaging a ball nut. The member 128 and the corresponding nut remain stationary while allowing the screw 130 to move relative to the nut as the screw rotate. The latter is suitably journaled at its opposite ends so that it freely rotates in response to motor means 132, such as a reversible drive electric stepper motor, mounted to the portion 100 of the annular frame, without moving longitudinally within the journals so that as the screw rotates the entire frame (and therefore the entire gantry assembly) pivots about the arms 114. The upper end of arm 128 is adapted to accommodate two-way movement along a track generally defined by screw element 130. The movement track has a length somewhat less than the width of gantry assembly 12. Limited vertical movement of the end of screw element 130 opposite motor 132 is provided by vertically extending slot 134 along the inner side of rear face 102 so as to permit pivotable movement of the gantry assembly about the arms 114. More specifically, as seen in FIG. 6, the longitudinal axis of screw element 130 may be tilted at an acute angle to the horizontal as a function of where along its length it is engaged by arm 128 so, that as the gantry assembly pivots about the arms 114, any lateral movement of the screw will be accommodated. As motor 132 rotates screw element 130 in a clockwise direction, the gantry frame pivots about the arms 114 in a first direction. Conversely, as motor 132 rotates screw element 130 in a counterclockwise direction, the gantry assembly pivots about the arms 114 in a second, opposite direction. Because arm 128 is fixed, rotational movement of the screw element 130 results in tilting or untilting gantry assembly 12 and, therefore, the pivot axis of the tomography apparatus is defined by the longitudinal axes of the two arms 114. Electrical monitoring means may be used to precisely control the desired angle of tilting for a particular scanning procedure.

Thus, the apparatus of this invention comprises a readily transportable tomography system which accommodates the needs of the patient and the physician in a variety of medical environments where prior art systems, because of size, weight, or physical configuration, would have been difficult if not impossible to use. The tomography system of this invention can be utilized, for example, in the operating theater with minimal disruption to the surgical procedure in progress. With the present invention, no movement of either the patient or the patient table is required. Once the cart apparatus carrying the tomography system is generally positioned vis-a-vis the patient, the displacement and tilting mechanisms of this invention can be used to precisely control and monitor the plane of an X-ray scan.

Since other changes may be made in the above-described apparatus and method without departing from the scope of the invention herein involved, it is intended that all matter contained in the above description shall be interpreted in an illustrative and not in a limiting sense.

Having described the invention, what is claimed is:

1. An X-ray tomographic scan apparatus of the type comprising: (a) an X-ray source and X-ray detection means for use in forming a tomographic image; (b) a gantry assembly including (i) a non-rotatable support, and (ii) means for supporting at least said X-ray source for rotation within a scanning plane about a rotation axis relative to said non-rotatable support so as to perform a tomographic scan; (c) an object support for supporting an object positioned in the scanning plane during a tomographic scan; said apparatus further comprising:

gantry assembly support means, capable of being fixed relative to said object support, for supporting said gantry assembly so that said gantry assembly is movable along a longitudinal axis substantially parallel to the object support, said gantry support means comprising at least two support surfaces positioned respectively on opposite sides of said gantry assembly;

a pair of supports disposed on diametrically opposite sides of said gantry assembly for supporting said gantry assembly respectively on said two support surfaces; and means, coupled between said pair of said supports and said two support surfaces for moving sad gantry assembly relative to said gantry assembly support means and said object support along said longitudinal axis so as to precisely control the position of the gantry assembly relative to the object support.

2. An X-ray tomographic apparatus according to claim 1, wherein said means for moving said gantry assembly relative to said gantry assembly support means and said object support along said longitudinal axis includes means for measuring the relative displacement of said gantry assembly relative to said gantry assembly support means and said object support.

3. An X-ray tomographic apparatus according to claim 1, wherein said object support is an patient table having an elongated dimension, said apparatus further including base support means including means for defining said two support surfaces, a first plurality of wheels for supporting said base support means so that said gantry assembly and said gantry assembly support means are easily movable, and a second plurality of wheels for supporting said patient table so that said patient table is easily movable, and means for fixing said patient table relative to said base support means so that said longitudinal axis is substantially parallel to the elongated dimension of said table.

4. An X-ray tomographic apparatus according to claim 3, wherein said pair of supports includes a pair of arms disposed on diametrically opposite sides of said gantry assembly and respectively supported by said two support surfaces.

5. An X-ray tomographic apparatus according to claim 4, when said arms pivotably support said gantry assembly on said two support surfaces.

6. An X-ray tomographic apparatus according to claim 4, wherein said means for selectively moving said gantry assembly relative to said gantry assembly support means and said patient table includes longitudinal translation means for coupling each of said arms to a respective support surface.

7. An X-ray tomographic apparatus according to claim 6, wherein said longitudinal translation means includes a ball screw and nut assembly including a ball screw and ball nut for coupling each of said arms to a respective support surface.

8. An X-ray tomographic apparatus according to claim 7, wherein each of said ball screws is disposed on a respective one of said support surfaces so as to be substantially parallel with said longitudinal axis.

9. An X-ray tomographic apparatus according to claim 7, further including means for accommodating a predetermined amount of non-parallelism between said ball screws.

10. An X-ray tomographic apparatus according to claim 7, further including means for separately driving each of said ball screws in synchronism so that when said gantry assembly is displaced relative to each of said support surfaces the displacement is the same for each of said support surfaces.

11. An X-ray tomographic apparatus according to claim 10, wherein said means for separately driving each of said ball screws includes a stepper motor, and means for simultaneously operating said stepper motors so that they are driven at the same speed.

12. An X-ray tomographic apparatus according to claim 11, wherein said stepper motors are reversible so that each of said ball screws can be driven in either rotational direction.

13. An X-ray tomographic apparatus according to claim 1, further including means for pivoting said gantry assembly relative to said gantry assembly support means about an axis substantially normal to said longitudinal axis so that said scanning plane can be pivotably moved to an adjustable angle to the longitudinal axis.

14. An X-ray tomographic apparatus according to claim 13, wherein said pair of supports includes a pair of arms disposed on diametrically opposite ides of said gantry assembly and respectively supported by said two support surfaces, further wherein said means for pivoting said gantry assembly comprises means for pivoting said gantry assembly about said arms.

15. An X-ray tomographic apparatus according to claim 14, further including means for controlling and measuring the angle of said gantry assembly relative to said longitudinal axis.

16. An X-ray tomographic apparatus according to claim 15, wherein said means for pivoting said gantry assembly about said arms includes a screw element coupled to said gantry assembly support means and a pivotable arm member coupled to said gantry assembly, wherein one end of said arm engages said screw element so as to move along said screw element as said screw element rotates, and the other end of said arm is coupled to said non-rotatable support.

17. An X-ray tomographic apparatus according to claim 1, wherein said object support is a patient table.

18. An X-ray tomographic apparatus according to claim 1, wherein said object support is a patient chair.

19. An X-ray tomographic apparatus according to claim 1, wherein said object support includes a support for supporting a limb.

20. X-ray tomography apparatus comprising in combination:

(a) an object support having an elongated dimension;

(b) X-ray source and X-rays detection means for use in forming a tomographic image;

(c) an annular gantry assembly comprising a gantry frame, and a rotatable disk for rotatably supporting at least the X-ray source so that said X-ray source rotates about an axis of rotation relative to the gantry frame during operation;

(d) means for rotating said disk about said axis of rotation so as to define a scanning plane;

(e) cart means for portably supporting said gantry assembly, said cart means including two upwardly extending members flanking the outer circumferential wall of said gantry assembly;

(f) lateral displacement means for coupling said gantry assembly to said upwardly extending members so that said gantry assembly can selectively move in each of two opposite directions, relative to said two upwardly extending members substantially parallel to the elongated dimension of said object support; and (g) activation means for activating said lateral displacement means.

21. Apparatus according to claim 20, further comprising control means for monitoring and adjusting the position of said gantry assembly relative to said cart.

22. Apparatus according to claim 21, wherein said control means comprises potentiometer means coupled to said activation means.

23. Apparatus according to claim 20, wherein said activation means comprises at least one reversible motor and said lateral displacement means comprises at least a first screw means coupled to said motor and at least fit first displacement member fixedly couple to said gantry assembly, farther wherein said first screw means engages said first displacement member such that rotation of said screws means by said motor results in movement of said first displacement member parallel to said elongated dimension of said object support.

24. Apparatus according to claim 23, wherein said cart means includes rolling means so that said gantry assembly can be transported by rolling said cart.

25. Apparatus according to claim 24, wherein said rolling means comprises a plurality of wheels.

26. Apparatus according to clam 20, further including means for tilting said gantry assembly so as to tilt said scanning plane relative to the elongated direction of said object support.

27. Apparatus according to claim 26, wherein said tilting means comprises angular displacement means for two-way movement of a second displacement member relative to said gantry assembly along a track generally parallel to said axis of rotation, linkage means for coupling said second displacement member to said gantry assembly, and second activation means for activating said angular displacement means.

28. Apparatus according to claim 27, wherein said second activation means comprises a reversible motor and said angular displacement means comprises second screw means coupled to said motor, further wherein said second screw means engages said second displacement member such that rotation of said screw means by said motor results in movement of said second displacement member along said second track.

29. X-ray tomography apparatus comprising in combination:

(A) an object support having an elongated dimension;

(B) a gantry assembly including:

(a) X-ray source and X-ray detection means for use in forming a tomographic image;

(b) an annular gantry assembly comprising a gantry frame, and a rotatable disk for rotatably supporting at least the X-ray source so that said X-ray source rotates about an axis of rotation relative to the gantry frame during operation; and (c) means for rotating said disk about said as of rotation so as to define a scanning plane;

(C) cart means for supporting said gantry assembly, said cart means comprising:

(a) support wheels for transporting said gantry assembly; and (b) two upwardly extending members flanking diametrically opposite sides of the outer circumferential wall of said gantry assembly, said extending members supporting said gantry assembly for lateral movement in a direction parallel to the object support and for pivotal movement about a pivot axis normal to the direction of said lateral movement;

(D) lateral displacement means for coupling said gantry assembly to said upwardly extending members so that said gantry assembly can selectively move in each of two opposite directions, relative to said two upwardly extending members in a direction substantially parallel to the object support; and (E) means for selectively securing said object to said cart means so that a tomographic scan can be made of a portion of an object supported by said object support.

30. An X-ray tomography apparatus according to claim 29 further comprising a patient limb support for supporting only a portion of a patient.

31. An X-ray tomography apparatus according to claim 30, further including a chair for supporting a patient whose limb is supported by said patient limb support.

32. An X-ray tomography apparatus according to claim 30, further wherein said lateral displacement means is selectively movable in each of two opposite directions, relative to said patient limb support.

*33. A method of generating volumetric image data of an object, said method comprising the steps of:*

*providing a tomographic scanning system including (i) an X-ray source and (ii) an X-ray detector for detecting X-rays emitted by the X-ray source and for generating scan data as a function of the detected X-rays, at least one of the X-ray source and detector being rotatable about a rotation axis to generate the scan data;*

*successively incrementally positioning the X-ray source and X-ray detector stepwise at a plurality of successive discrete positions along the rotation axis;*

*at each of the plurality of discrete positions along the rotation axis, generating a set of scan data for the object; and*

*generating the volumetric image data for the object using the sets of scan data generated at the plurality of successive discrete positions.*

*34. A method according to claim 33, further including the step of generating a volumetric image of the object using the volumetric image data.*

*35. A method according to claim 33, further including the step of translating the X-ray source and X-ray detector along the rotation axis to each of the successive discrete positions prior to rotating at least one of the X-ray source and detector at each such discrete position to generate the scan data for the discrete position.*

*36. A method of claim 33, wherein the object is a medical patient undergoing tomographic examination.*

*37. A method of claim 33, wherein at least the X-ray source is mounted on a rotatable gantry of the X-ray tomography system, said rotatable gantry being translatable along the rotation axis.*

*38. An X-ray tomography apparatus for generating volumetric image data of an object, said apparatus comprising:*

*a tomographic scanning system including (i) an X-ray source and (ii) an X-ray detector for detecting X-rays emitted by the X-ray source and for generating scan data as a function of the detected X-rays, at least one of the X-ray source and detector being rotatable about a rotation axis to generate the scan data;*

*means for successively incrementally positioning the X-ray source and X-ray detector system step-wise at a plurality of successive discrete positions along the rotation axis;*

*means for generating a set of scan data for the object at each of the plurality of discrete positions along the rotation axis; and*

*means for generating the volumetric image data for the object using the sets of scan data generated at the plurality of successive discrete positions.*

*39. Apparatus according to claim 38, further including means for generating a volumetric image of the object using the volumetric scan data.*

*40. Apparatus according to claim 38, further including means for translating the X-ray source and X-ray detector along the rotation axis to each of the successive discrete positions prior to rotating at least one of the X-ray source and detector at each such discrete position to generate the scan data for the discrete position.*

*41. Apparatus according to claim 40, further comprising a rotatable gantry on which at least the X-ray source is mounted; and wherein the means for translating the X-ray source and the X-ray detector along the rotation axis comprises means for translating the rotatable gantry along the rotation axis.*

*42. Apparatus according to claim 38, wherein the object is a medical patient undergoing tomographic examination.*

*43. An X-ray tomographic scan apparatus of the type comprising: (a) an X-ray source and X-ray detection means for use in forming a tomographic image; (b) a gantry assembly including (i) a non-rotatable support, and (ii) means for supporting at least said X-ray source for rotation within a scanning plane about a rotation axis relative to said non-rotatable support so as to perform a tomographic scan; (c) coupling means for coupling the gantry assembly to an object support for supporting an object positioned in the scanning plane during a tomographic scan; said apparatus further comprising:*

*gantry assembly support means, capable of being fixed relative to said object support, for supporting said gantry assembly so that said gantry assembly is movable along a longitudinal axis positionable substantially parallel to the object support, said gantry support*

*means comprising at least two support surfaces positioned respectively on opposite sides of said gantry assembly;*

*a pair of supports disposed on diametrically opposite sides of said gantry assembly for supporting said gantry assembly respectively on said two support surfaces; and*

*means, coupled between said pair of said supports and said two support surfaces, for moving said gantry assembly relative to said gantry assembly support means along said longitudinal axis so as to precisely control the position of the gantry assembly relative to the object support when the gantry assembly is coupled to the object support.*

*44. An X-ray tomographic apparatus according to claim 43, wherein said means for moving said gantry assembly relative to said gantry assembly support means along said longitudinal axis includes means for measuring the relative displacement of said gantry assembly relative to said gantry assembly support means.*

*45. An X-ray tomographic apparatus according to claim 43, wherein said object support is a patient table having an elongated dimension positionable along said longitudinal axis.*

*46. An X-ray tomographic apparatus according to claim 45, further comprising base support means including means for defining said two support surfaces, a first plurality of wheels for supporting said base support means so that said gantry assembly and said gantry assembly support means are easily movable, and a second plurality of wheels for supporting said patient table so that said patient table is easily movable, and means for fixing said patient table relative to said base support means so that said longitudinal axis is substantially parallel to the elongated dimension of said table.*

*47. An X-ray tomographic apparatus according to claim 43, wherein said pair of supports includes a pair of arms disposed on diametrically opposite sides of said gantry assembly and respectively supported by said two support surfaces.*

*48. An X-ray tomographic apparatus according to claim 47, wherein said arms pivotably support said gantry assembly on said two support surfaces.*

*49. An X-ray tomographic apparatus according to claim 47, wherein said means for selectively moving said gantry assembly relative to said gantry assembly support means includes longitudinal translation means for coupling each of said arms to a respective support surface.*

*50. An X-ray tomographic apparatus according to claim 49, wherein said longitudinal translation means includes a ball screw and nut assembly including a ball screw and ball nut for coupling each of said arms to a respective support surface.*

*51. An X-ray tomographic apparatus according to claim 50, wherein each of said ball screws is disposed on a respective one of said support surfaces so as to be substantially parallel with said longitudinal axis.*

*52. An X-ray tomographic apparatus according to claim 50, further including means for accomodating a predetermined amount of non-parallelism between said ball screws.*

*53. An X-ray tomographic apparatus according to claim 43, further including means for pivoting said gantry assembly relative to said gantry assembly support means about an axis substantially normal to said longitudinal axis so that said scanning plane can be pivotably moved to an adjustable angle to the longitudinal axis.*

*54. An X-ray tomographic apparatus according to claim 53, wherein said pair of supports includes a pair of arms disposed on diametrically opposite sides of said gantry assembly and respectively supported by said two support surfaces, further wherein said means for pivoting said gantry assembly comprises means for pivoting said gantry assembly about said arms.*

*55. An X-ray tomographic apparatus according to claim 54, further including means for controlling and measuring the angle of said gantry assembly relative to said longitudinal axis.*

*56. An X-ray tomographic apparatus according to claim 55, wherein said means for pivoting said gantry assembly about said arms includes a screw element coupled to said gantry assembly support means and a pivotable arm member coupled to said gantry assembly, wherein one end of said arm engages said screw element so as to move alone said screw element as said screw element rotates, and the other end of said arm is coupled to said non-rotatable support.*

*57. An X-ray tomographic apparatus according to claim 43, wherein said object support is a patient chair.*

*58. An X-ray tomographic apparatus according to claim 43, wherein said object support includes a support for supporting a limb.*

* * * * *

UNITED STATES PATENT AND TRADEMARK OFFICE

CERTIFICATE OF CORRECTION

PATENT NO. : Re. 36,415

DATED : November 30, 1999

INVENTOR(S) : Gilbert W. McKenna

It is certified that error appears in the above-identified patent and that said Letters Patent is hereby corrected as shown below:

Column 10, line 49, add -- ' -- after "surfaces".

Column 11, line 53, change "ides" to –sides--.

Column 12, line 43, change "fit" to –a--.

Column 12, line 44, change "couple" to –coupled--.

Column 13, line 18, change "as" to –axis—.

Column 16, line 37, change "alone" to –along--.

Signed and Sealed this

Nineteenth Day of September, 2000

*Attest:*

Q. TODD DICKINSON

*Attesting Officer*

*Director of Patents and Trademarks*